United States Patent [19]

Nickell

[11] 4,405,361
[45] Sep. 20, 1983

[54] METHOD OF INCREASING THE YIELD OF SUGAR OBTAINED FROM SUGAR CANE

[75] Inventor: Louis G. Nickell, Chicago, Ill.

[73] Assignee: Velsicol Chemical Corporation, Chicago, Ill.

[21] Appl. No.: 455,180

[22] Filed: Jan. 3, 1983

Related U.S. Application Data

[63] Continuation-in-part of Ser. No. 365,862, Apr. 5, 1982, abandoned.

[51] Int. Cl.³ ............................................. A01N 33/02
[52] U.S. Cl. .......................................... 71/121; 71/76; 71/27; 127/42
[58] Field of Search ................... 71/27, 106, 107, 113, 71/121; 127/42

[56] References Cited

U.S. PATENT DOCUMENTS

| 3,482,961 | 12/1969 | Nickell et al. | 71/121 |
| 3,870,503 | 3/1975 | Nickell | 71/106 |
| 4,284,425 | 8/1981 | Luteri | 71/27 |
| 4,294,604 | 10/1981 | Evrard | 71/27 |
| 4,313,752 | 2/1982 | Siemer | 71/27 |

Primary Examiner—Ferris H. Lander
Attorney, Agent, or Firm—Robert J. Schwarz

[57] ABSTRACT

This invention discloses a method of increasing the sugar content in sugar cane with the use of the compound N,N-dimethyl-N-hexadecyl-N-2-propenylammonium bromide.

4 Claims, No Drawings

METHOD OF INCREASING THE YIELD OF SUGAR OBTAINED FROM SUGAR CANE

This application is a continuation-in-part of my co-pending application, Ser. No. 365,862, filed Apr. 5, 1982, and now abandoned.

This invention relates to a method of increasing the yield of sugar obtained from sugar cane and more particularly relates to a method of increasing the recoverable sugar in sugar cane by treating the sugar cane plant during its maturation with a certain benzoic acid compound.

A variety of plant growth regulators, stimulants and promoters have been tried in the past in attempts to increase the yields of cultivated crops. These attempts have met with varying success, but have generally attained limited commercial significance. One particular crop which has been given increased attention for the purpose of augmenting yields is sugar cane. Accordingly, it is an object of the present invention to provide a new method of increasing the yield of sugar obtained from sugar cane.

It has been found that the recovery of sugar from sugar cane can be substantially increased through the use of N,N-dimethyl-N-hexadecyl-N-2-propenylammonium bromide. Thus, one embodiment of the present invention resides in a method of increasing the recoverable sugar contained in sugar cane which comprises contacting the sugar cane plant during maturation with an effective amount of N,N-dimethyl-N-hexadecyl-N-2-propenylammonium bromide.

To effect the method of this invention, sugar cane is treated at a late stage of development. This treatment is carried out during that stage of development of the sugar cane when most of the sugar storage takes place. Thus, under normal growing conditions and common cultivation practices, the active compound of this invention can be applied to the sugar cane during the period of from about 2 to about 14 weeks before harvesting.

The amount of active compound required to effectively increase the recoverable sugar from sugar cane can vary somewhat depending on such factors as the time of application, the weather, crop density, method of application and the like. Generally, an amount of at least 0.1 pounds per acre and preferably an amount of from 0.2 pounds per acre to about 2 pounds per acre can be used. While an amount greater than those mentioned can be used, they will not result in an advantage that would warrant their expense and are therefore, not practical.

For practical use in treating sugar cane, the active compound of this invention is generally incorporated into compositions of formulations which comprise an inert carrier and an effective amount of the compound. The compositions enable the active compound to be conveniently applied to the sugar cane at the desired rate. The formulations can be liquid formulations such as emulsifiable concentrates or solutions or solid formulations such as dusts, granules or wettable powders.

The preferred compositions are liquid formulations, particularly aqueous solutions which may optionally contain surface active agents or emulsifiable concentrates. Emulsifiable concentrates comprise the active compound according to this invention and as the inert carrier, a solvent and an emulsifier. Such emulsifiable concentrates can be extended with water and/or oil to any desired concentration of active compound for application as sprays to the sugar cane. The emulsifier most commonly used in these concentrates are non-ionic or mixtures of non-ionic with anionic surfactive emulsifier. Such emulsifiable concentrates can be extended with water and/or oil to any desired concentration of active compound for application as sprays to the sugar cane. The emulsifier most commonly used in these concentrates are nonionic or mixtures of nonionic with anionic surface-active agents. With the use of some emulsifier systems, an inverted emulsion (water-in-oil) can be prepared.

Typical formulations according to the present invention useful for increasing the recoverable sugar in sugar cane are illustrated in the following examples wherein the quantities are given in parts by weight.

EXAMPLE 1

Preparation of a Solution

The following ingredients are combined and stirred until dissolution is effected.

| | |
|---|---|
| N,N—dimethyl-N—hexadecyl-N—2-propenylammonium bromide | 5 |
| Water | 40 |
| Ethoxylated nonylphenol surfactant | 2.5 |

EXAMPLE 2

Preparation of an Emulsifiable Concentrate

The following ingredients are blended thoroughly until a homogeneous liquid concentrate is obtained. This concentrate is mixed with water to give an aqueous dispersion containing the desired concentration of the active ingredients for use as a spray.

| | |
|---|---|
| N,N—dimethyl-N—hexadecyl-N—2-propenylammonium bromide | 25 |
| Sodium lauryl sulfate | 2 |
| Sodium lignin sulfate | 3 |
| Aromatic naphtha | 70 |

EXAMPLE 3

Preparation of a Wettable Powder

The following components are mixed intimately in conventional mixing or blending equipment and are then ground to a powder having a particle size of less than about 50 microns. The finished powder is dispersed in water to give the desired concentration of active compound for application to the sugar cane.

| | |
|---|---|
| N,N—dimethyl-N—hexadecyl-N—2-propenylammonium bromide | 50 |
| Fuller's earth | 47 |
| Sodium lauryl sulfate | 2.5 |
| Methyl cellulose | 0.5 |

EXAMPLE 4

Preparation of a Dust

The following ingredients are mixed thoroughly and are then ground to an average particle size of less than about 50 microns to give a dust suitable for application with conventional dusting equipment.

| | |
|---|---|
| N,N—dimethyl-N—hexadecyl-N—2-propenylammonium bromide | 10 |
| Powdered talc | 90 |

The effectiveness of the compounds of this invention for increasing the recoverable sugar from sugar cane was demonstrated in field tests by applying a solution in acetone diluted for application to the various indicated application rates. The test compound was applied at each rate on the spindle area of each of 20 stalks of sugar cane in a field in Hawaii, using a syringe with a fine needle as the applicator. A set of ten untreated stalks were also harvested as a control.

The top 14 joints of the treated cane, as well as those of the controls, were removed, combined and analyzed for juice purity and pol percent cane, followed the "press method" developed and described by T. Tanimoto, Hawaiian Planters Record, 57, 133 (1964). Pol percent cane is a polarimetric determination and equals the percentage of sucrose if the latter is the only substance in the solution which will rotate the plane of polarized light. The pol percent cane is a standard method of determining the sucrose content of sugar cane.

The effectiveness of the compounds of this invention for increasing the yield of sugar obtained from sugar cane is demonstrated by the data set out in the following tables. Each table represents a separate experiment conducted at a different time. The cane was harvested eight weeks after application of the test compound.

TABLE 1

| TEST NO. | RATE IN LBS./ACRE | PURITY | POL % CANE |
|---|---|---|---|
| 1 | 1 | 89.25 | 13.87 |
| — | 0 (Control) | 86.49 | 12.17 |
| 2 | 1 | 82.65 | 12.19 |
| — | 0 (Control) | 77.63 | 10.92 |
| 3 | 1 | 77.20 | 10.26 |
| — | 0 (Control) | 77.60 | 10.43 |

I claim:

1. A method of increasing the recoverable sugar contained in sugar cane which comprises contacting the sugar cane plant with an effective amount of the compound, N,N-dimethyl-N-hexadecyl-N-2-propenylammonium bromide.

2. The method of claim 1 wherein the sugar cane is contacted with about 0.2 to about 2 pounds per acre of said compound.

3. The method of claim 1 wherein the sugar cane is contacted with said compound during the period of from about 2 to about 14 weeks before harvest.

4. The method of claim 1 wherein the sugar cane is contacted with about 0.1 to about 10 pounds per acre with said compound during the period of from about 2 to about 14 weeks before harvest.

* * * * *